(12) United States Patent
Reinius

(10) Patent No.: US 10,039,677 B2
(45) Date of Patent: Aug. 7, 2018

(54) PLASTER DISPENSER AND FIRST AID KIT CONTAINER

(71) Applicant: Orkla Care AB, Upplands Väsby (SE)

(72) Inventor: Pelle Reinius, Enskede Gård (SE)

(73) Assignee: ORKLA CARE AB, Upplands Väsby (SE)

( * ) Notice: Subject to any disclaimer, the term of this patent is extended or adjusted under 35 U.S.C. 154(b) by 33 days.

(21) Appl. No.: 15/166,606

(22) Filed: May 27, 2016

(65) Prior Publication Data

US 2016/0338885 A1 Nov. 24, 2016

(30) Foreign Application Priority Data

May 28, 2015 (SE) ...................................... 1550692

(51) Int. Cl.
| | |
|---|---|
| A61B 17/06 | (2006.01) |
| A61B 19/02 | (2006.01) |
| A61L 15/00 | (2006.01) |
| A61F 15/00 | (2006.01) |
| A61F 17/00 | (2006.01) |
| B65D 83/08 | (2006.01) |

(52) U.S. Cl.
CPC ............ *A61F 15/001* (2013.01); *A61F 17/00* (2013.01); *B65D 83/0805* (2013.01)

(58) Field of Classification Search
CPC ...... A61F 15/001; A61F 17/00; A61F 13/551; A61F 13/00; B65D 83/0805
USPC ....... 206/440, 214, 570, 574, 582, 229, 233, 206/349; 221/67, 68
See application file for complete search history.

(56) References Cited

U.S. PATENT DOCUMENTS

| | | | | |
|---|---|---|---|---|
| 4,807,753 | A  * | 2/1989 | Goldstein | A61F 15/002 206/390 |
| 5,178,282 | A  * | 1/1993 | Williams | A61B 50/30 206/363 |
| 8,047,399 | B1 * | 11/2011 | Sexton | A61F 15/001 206/440 |
| 2005/0029155 | A1* | 2/2005 | Edwards | A61J 1/03 206/570 |
| 2005/0178783 | A1* | 8/2005 | Pastan | A61F 15/001 221/58 |
| 2005/0194391 | A1* | 9/2005 | Domke | A61F 15/001 220/835 |
| 2005/0258183 | A1* | 11/2005 | Fienup | A61F 15/001 221/56 |
| 2012/0285981 | A1* | 11/2012 | Benedetti | A61F 15/001 221/92 |
| 2013/0098938 | A1* | 4/2013 | Efthimiadis | A47K 10/421 221/45 |

(Continued)

FOREIGN PATENT DOCUMENTS

WO 2006078201 A1 7/2006

*Primary Examiner* — Rafael Ortiz

(74) *Attorney, Agent, or Firm* — Tucker Ellis LLP

(57) ABSTRACT

A plaster dispenser for holding a plaster pack from which plasters may be removed individually. A rear wall of the dispenser limits movement of the plaster pack in a rearward direction; and first and second shoulders of an openable and closeable gate limit movement of the pack in a forward direction. When the gate is opened, movement of the pack is no longer limited in the forward direction, to make it possible to remove the plaster pack from the dispenser. The dispenser may from part of a first aid kit container.

10 Claims, 6 Drawing Sheets

(56) References Cited

U.S. PATENT DOCUMENTS

2015/0351965 A1\* 12/2015 Umentum ................. A61F 9/04
                                                    221/92

\* cited by examiner

PLASTER DISPENSER AND FIRST AID KIT CONTAINER

RELATED APPLICATION DATA

This application claims the benefit of Swedish Patent Application No. 1550692-6, filed May 28, 2015, the disclosure of which is incorporated herein by reference in its entirety.

FIELD OF THE INVENTION

This invention relates to a dispenser for plasters, i.e. adhesive bandages for applying on minor wounds such as cuts, and a first aid kit container with such a dispenser.

BACKGROUND

Plasters—self-adhesive bandages for applying on minor wounds, such as small cuts—may be provided from plaster packs which comprise pockets that hold a number of plasters in a "booklet"-like fashion. Such plaster packs are well-known. A plaster pack may contain plasters in different sizes and materials.

Plasters in a plaster pack may be dispensed from a wall mounted dispenser that holds the plaster pack. The wall mounted dispensers are usually provided at workplaces, schools, etc. where the plasters will then be easily available in the case of a minor injury. The dispenser holds the plaster pack so that users can pull plasters from the plaster packs when they need a plaster.

When a plaster pack in a dispenser has been emptied of its contents, the empty pack is to be replaced with a new one.

One problem with plaster dispensers for plaster packs is that the plaster pack—which contains a number of plasters—is susceptible to theft when it is in the dispenser. In order to solve this problem WO2006078201 discloses a wall-mounted plaster dispenser where the plaster pack cannot be removed in the direction of pulling out the plasters. Instead, the empty plaster pack is removed and replaced by accessing a space behind the dispenser. This may involve unlocking a door or accessing the space behind the dispenser. Alternatively a key is used to displace the plaster pack so that it can be removed.

One problem associated with WO2006078201 is that it is rather cumbersome to change the plaster pack. This is necessary since the problems solved by WO2006078201 is to avoid theft of the plaster pack.

The key solution has the disadvantage that the key can be misplaced. In general there is a need to improve the manner in which plaster packs in dispenser are replaced.

Moreover, the plaster dispenser in WO2006078201 is rather bulky and intended to be mounted on a wall. Therefore it not suitable to be used in cars, small boats, on aircraft etc.

BRIEF DESCRIPTION OF DRAWINGS

The invention will now be described in more detail by means of exemplary embodiments and with reference to the accompanying drawings, in which.

SUMMARY OF INVENTION

Figure 1A:
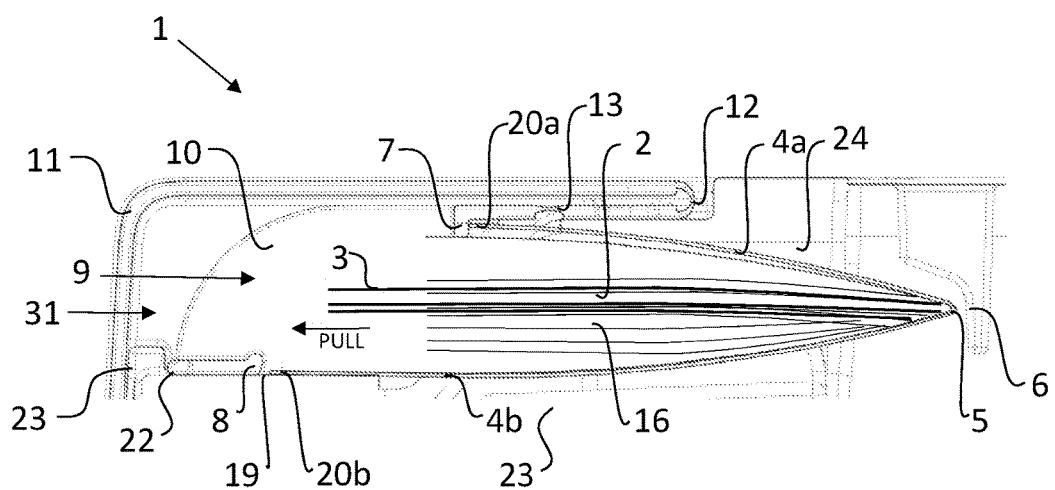
FIG. 1a is a schematic cross sections of a plaster dispenser seen in the direction of the main axis and where the front direction of the dispenser is to the left.

In a first aspect there is provided a plaster dispenser for holding a plaster pack and for removing plasters individually from said plaster pack, which plaster pack comprises a plurality of plasters, each accommodated in a pocket, wherein the pockets are directed in generally the same direction and located between first and second sheets, said sheets and pockets being connected along an edge that extends perpendicularly to the longitudinal direction of respective pockets, said edge being located opposite to the opening of the pockets, where the plaster dispenser has at least one compartment for holding a plaster pack, said compartment having a main opening for inserting and removing a plaster pack, said opening defining a front direction of the dispenser, where the plaster dispenser comprises: a) a first wall limiting the movement of the plaster pack in a direction opposite to the front direction, b) a first shoulder limiting the movement of the first sheet in the front direction; c) a second shoulder limiting the movement of the second sheet in the front direction; d) an opening for removing individual plasters from the plaster pack in the front direction; characterized in that the dispenser comprises e) a gate comprising said opening for removing individual plasters, said gate further comprising said first and second shoulders, wherein the gate can be opened or removed to make it possible to remove the plaster pack from the dispenser.

One advantage with the inventive dispenser is that it is easy to replace the plaster pack, since it is not necessary to access the dispenser from the back side or unlocking a door. Instead the plasters pack is removed and replaced from the same direction from which plasters are dispensed. This does away with the need for access to the back side of the dispenser according to prior art. Moreover, no key is required when replacing the plaster pack.

The gate may have a hinge for opening and closing the gate. This has the advantage that the gate is attached to the dispenser so it does not get misplaced.

The dispenser may have a lid that is able to cover the opening for removing plasters and the gate. This has the advantage of protecting the plasters from dust and moisture. The lid may also cover the main opening for replacing the plaster pack. The lid may have a hinge. An advantage with this is that the lid does not get misplaced.

The hinge of the gate and the hinge of the lid may be parallel and arranged to open in the same direction. This has the advantage that the lid and the gate does not block access to the openings.

The lid and the gate may be made in one piece. The hinges may then be living hinges. This is an efficient way of manufacturing the lid and the gate, in order to obtain a dispenser that is flat and easy to integrate.

In a second aspect there is provided a first aid kit container comprising an integrated plaster dispenser according to the first aspect of the invention.

One advantage with this first aid kit container is that plasters are conveniently provided from a plaster pack connected to a first aid kit. The dispenser makes the plasters easy to grip and get ready for application to the wound. It is timesaving since only one adhesive-covering strip has to be removed. Moreover, the plaster pack keeps the plasters sorted by type, material and size and makes it easy for the user to choose the right type of plaster. Moreover, the comparatively small plasters are easy to locate compared to if they are lying loose together with other first aid kit components in a first aid kit container.

Moreover the first aid kit according to the invention provides a plaster pack where the previous, wall-mounted dispensers are not suitable, for example in cars, boats, etc. This makes the plaster pack available at mobile work places, for example in a first aid kit that can be placed in cars used by craftsmen, policemen, salespersons, farmers etc.

Also, the first aid kit container makes it possible to carry the plaster pack to the injured person who needs the plaster, rather than having the injured person located to the plaster pack.

In a preferred embodiment, the first aid kit container comprises a main compartment and individual plasters can be removed and the plaster pack can be replaced without accessing said main compartment. This can be achieved for example when the opening for removing plasters, the gate and the main opening are accessible without accessing the main compartment. Thus the plaster pack is available from the outside of the main compartment.

This avoids unnecessary opening of the main compartment of the first aid kit container when removing plasters or replacing the plaster pack and thereby protects the articles in the main space from contamination and dirt.

Moreover, sometimes the main compartment of first aid kit containers are equipped with a seal that is broken the first time the first aid kit is used. This is usually the case in for example Germany where the local DIN standard provides for a seal on first aid kits. The purpose of the seal is to indicate whether the first aid kit has ever been opened and thus may need replacement of consumed articles. Sometimes the entire first aid kit is replaced when the seal is broken, which is costly. Plasters are, overall, used more often than the first aid kit components intended for larger wounds such as compresses. Therefore it is an advantage that plasters and the plaster pack is accessible from outside of the main compartment of the first aid kit container, so that plasters can be used, and the empty/finished plaster pack can be replaced, without breaking the seal.

Also, the previously described key for removing the plaster pack is not suitable for use with a sealed first aid container kit because the key is not suitably placed in the main compartment (because of the seal) and is not suitable to be attached to the outside of the first aid kit (where it is easily accessible for someone who wants to steal the plaster pack.).

Where the first aid kit container has a lid, the dispenser is advantageously integrated in the lid. This makes it even easier to access the plasters.

In a second aspect of the invention there is provided a method of producing a first aid kit container comprising an integrated dispenser, the method comprising the steps of: a) forming a compartment forming part for the first aid kit container where the compartment forming part comprises a compartment for housing a plaster pack, b) forming a piece of polymer material comprising the gate and the lid of the dispenser, and c) attaching the piece to the lid so that a dispenser is formed, where steps a) and b) can be carried out in any order. The compartment forming part is preferably the lid.

DETAILED DESCRIPTION

FIG. 1a shows an embodiment of a dispenser 1 with the plaster pack 2 with plasters 3 in pockets 16. Plasters 3 typically comprise a rectangular strip of flexible textile or plastic material with an adhesive on one side. The pockets 16 are usually made from a paper or plastic material. Plasters 3 can be removed by a user by grabbing the protruding end of the plaster 3 and pulling to the left in FIG. 1a through opening 9 of dispenser (i.e. pulling in the front direction, see below) as indicated by arrow marked "PULL". Thus, the arrow marked "PULL" indicates the front direction. For the sake of simplicity only three plasters 3 are shown in FIG. 1a. However, the plaster pack 2 may comprise any suitable number of plasters 3. Some pockets 16 in FIG. 1a are shown empty and does not contain a plaster 3.

Figure 1B:
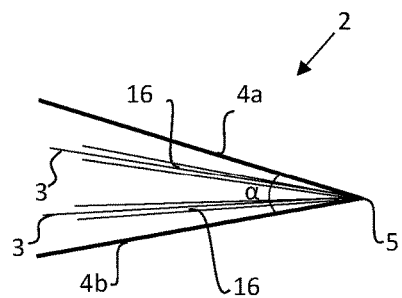
FIG. 1b is a schematic cross section of a plaster pack.

The plaster pack 2 shown in FIGS. 1a and 1b has the general shape of a booklet, where the pockets 16 are the "pages" of the booklet, such that at least some pockets 16 are stacked on top of each other. The plaster pack 2 has covering sheets 4a and 4b. The sheets 4a 4b are usually made in a stiff paper material or plastic material, such as for example thick paper or thin cardboard. The pockets 16 and the sheets 4a 4b are connected at an edge 5 which is the "spine" of the "booklet". The connecting edge 5 is opposite from the opening of the pockets 16. The connection between sheets 4a and 4b is hinged near the edge 5 such that the angle between sheets 4a and 4b can be changed in somewhat the same fashion as the cover of a booklet. The pockets 16 all have their openings in generally the same direction, away from the edge 5. "Generally same direction" shall mean that the angle α (FIG. 1b) between the sheets 4a and 4b—which limits the movement of the pockets 16—shall be at most 45°, more preferably at most 30° when the plaster pack 2 is inserted into the dispenser. When it is referred to the "general direction of the pockets 16" herein, it is meant the intermediate angle between sheets 4a and 4b, directed from the bottom of the pocket 16 towards the opening of the pockets 16.

One end of the plasters 3 protrudes from the pocket 16. The adhesive side of this end of the plaster 3 is typically covered by a protective sheet, which is removed after removing the plaster 3 from the plaster pack 2 but before applying the plaster 3 on the wound.

The main body 23 of the dispenser 1 has at least one compartment 24 for housing a plaster pack 2. The compartment 24 has a main opening 31 for inserting and removing the plaster pack 2. The plaster pack 2 is to be inserted into the dispenser 1 with the opening of the pockets 16 facing towards opening 9 (when gate 10 is closed) and main opening 31 and the edge 5 away from opening 9 and the main opening 31. Thus the plaster pack 2 may be removed from the dispenser in the front direction of the dispenser 1, which is the same direction that individual plasters are removed.

The dispenser 1 has a front direction which is to the left in FIG. 1a and 1b. The front direction is directed from innermost part of the compartment 24 towards main opening 31. Thus the front direction may be parallel to the general direction of the pockets 16 when the plaster pack 2 has been inserted in the dispenser 1.

The dispenser 1 is shown with the front direction in a horizontal orientation in the figures. However, the front direction may be any direction in relation to a horizontal direction. For example, the front direction may be vertical such that plasters 3 are removed from the dispenser 1 by pulling upwards or downwards. Having a vertical front direction may be particularly useful when the dispenser 1 or first aid kit container 17 (see below) is wall mounted.

The dispenser 1 has a main axis that is in the direction of viewing in FIGS. 1a and 1b. The main axis is perpendicular to the front direction of the dispenser 1, and is in the same plane as the front direction.

The main body 23 of dispenser 1 may have inner surfaces or walls for supporting the plaster pack 2 or a part of plaster pack 2. Such a surface may support at least a part of sheets 4a and/or 4b. In FIG. 1a it is shown how inner surface 19 supports sheet 4b. A side guide 29 (FIG. 2) may limit the sideways mobility of the plaster pack 2. Inner surfaces or walls may form compartment 24.

The dispenser 1 has an opening 9 from which users can access the plasters 3 and remove them by pulling them from the pockets 16. When a plaster 3 is pulled from the plaster pack 2, the plaster pack 2 is held in place in the dispenser 1 by first shoulder 7 that prevents sheet 4a from moving in the direction of pulling and second shoulder 8 that prevents sheet 4b from moving in the direction of pulling. Front edge 20a of sheet 4a will be stopped by rear surface of first shoulder 7 and front edge 20b of sheet 4b will be stopped by rear surface of second shoulder 8.

When inserting a plaster pack 2 into the dispenser 1 wall 6 receives edge 5 so that the plaster pack 2 does not move too far into the compartment 24 of dispenser 1. Wall 6 may have a groove for receiving edge 5.

Shoulders 7 and 8 and opening 9 are arranged on a gate 10. Gate 10 is able to cover a part of main opening 31. When gate 10 is closed, plasters 3 can be removed one by one trough opening 9 but the entire plaster pack 2 is locked between wall 6, and shoulders 7 and 8. In order to remove the plaster pack 2, the gate 10 is opened, as explained below.

Figure 2:
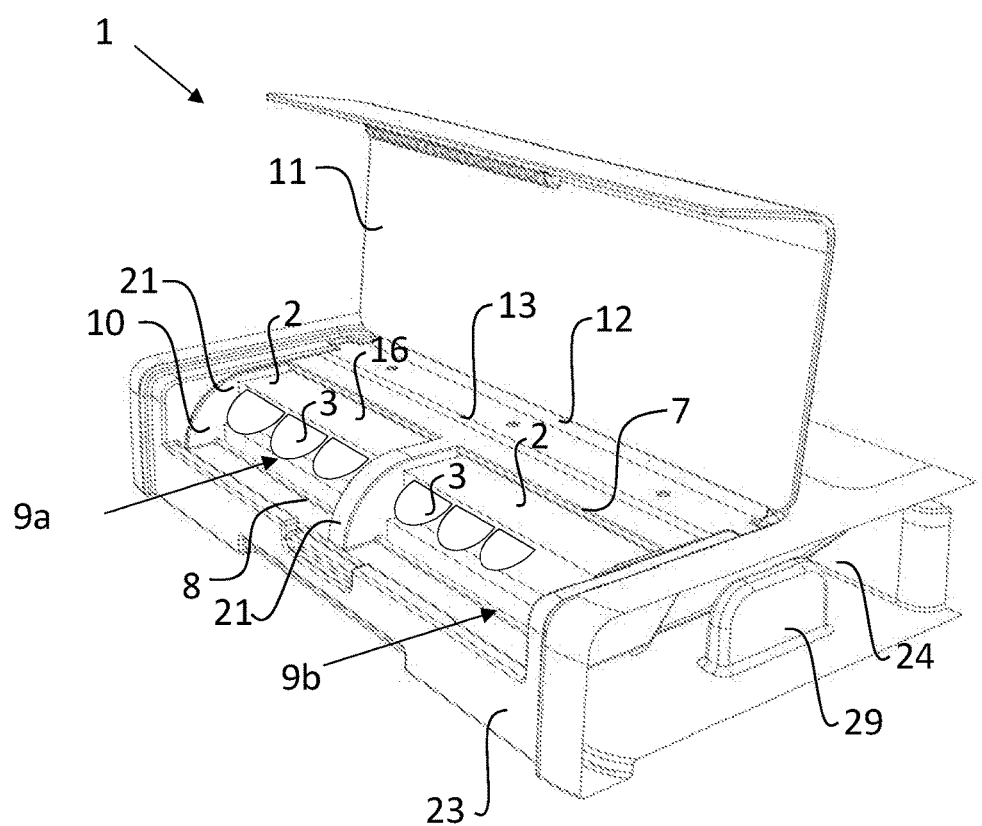
FIG. 2 is view of a plaster dispenser with the lid open.

FIG. 2 shows an embodiment of the plaster dispenser 1 from a perspective. The ends of the plasters 3 that protrude from the pockets 16 of the plaster pack 2 are visible in FIG. 2. The dispenser 1, shown in drawings 2, 3, 5, 6 and 8, has two compartments 24, each for holding one separate plaster pack 2. Plasters 3 can be accessed from each of openings 9a and 9b in gate 10 when plaster packs 2 are present in both compartments 24. However, the dispenser 2 may just as well have one compartment 24 and is then intended for one plaster pack 2. The two plaster packs 2 of FIG. 2 has a number of pockets with plasters arranged side-by-side, which is a common manner of arranging the plaster pack 2. The dispenser 1 may also have more than two compartments 24. When there is more than one compartment the compartments may have separate gates 10.

Figure 3:
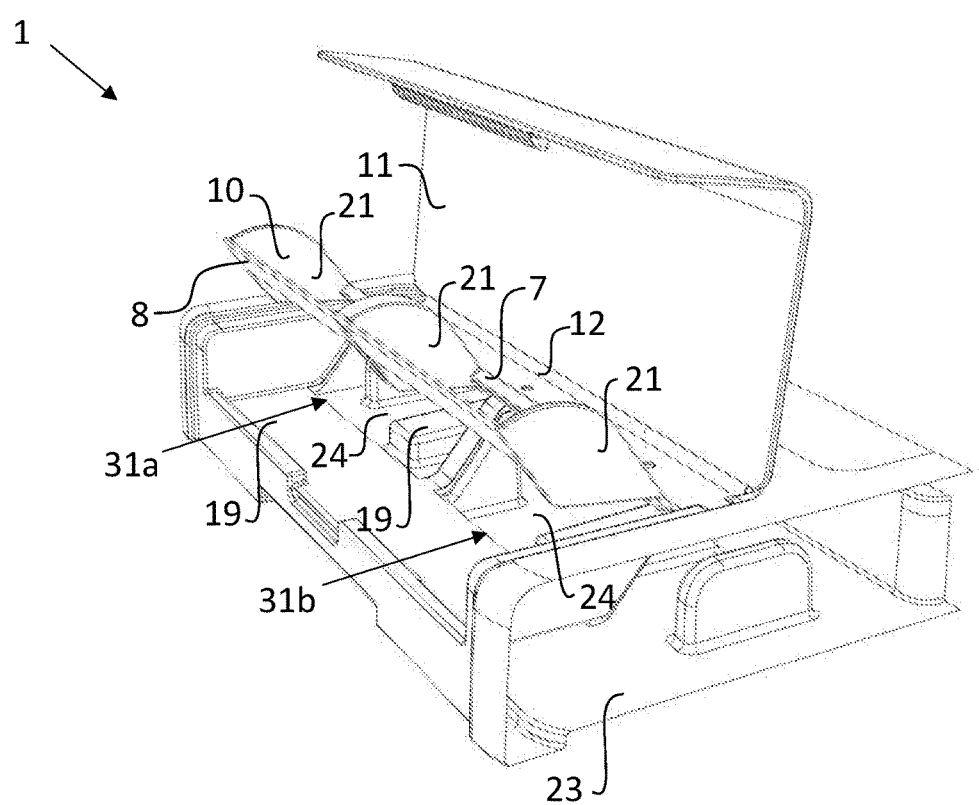
FIG. 3 is a view of a plaster dispenser with the gate and the lid open.

FIGS. 2 and 3 shows how shoulder 7 and shoulder 8 are connected with arms 21 to form gate 10. Gate 10 may have a hinge 13 allowing the gate 10 to be opened to enable insertion and removal of plaster pack 2. When the gate 10 has a hinge 13, it may snap lock to the main body of the dispenser 23 for example with a tight fit between front edge 22 of shoulder 8 and a part of main body 23 of dispenser 1. However, the gate 10 may lock to the main body of dispenser 23 with other types of locks, for example a spring powered mechanism. An advantage with the gate 10 having a hinge is that the gate 10 can be opened without detaching the gate 10 from the dispenser 1, lessening the risk of misplacement of gate 10.

The gate 10 may also be such that it is completely detachable from the main body 23 of dispenser 1 and then gate 10 may not have a hinge 13. Gate 10 may then, for example, be attached to the main body 23 of dispenser 1 with a snap-lock mechanism, a press fit or a spring loaded locking mechanism.

The dispenser may have a lid 11. An example of a lid 11 is shown in its open state in FIG. 2. The lid 11, when closed, covers the main opening 31, opening 9, the plaster pack 2 and the gate 10. The purpose of lid 11 is to protect the plasters 3 from dust, moisture and other contamination.

The lid 11 can be any type of lid. For example, it may be a roll-top type lid. Preferably, however, the lid 11 is a hinged lid. Then the lid 11 can be opened by means of hinge 12.

When both the gate 10 and the lid 11 have hinges, the hinges 12 and 13 may be non-parallel. For example hinge 12 and hinge 13 may be arranged at an angle of 90°. However, in a preferred embodiment the hinges 12 and 13 are parallel, and preferably they are parallel to the main axis of the dispenser 1 as shown in the figures.

The gate 10 and lid 11 are preferably hinged so that they swing in the same direction. This has the advantage that the gate 10 and the lid 11 does not interfere when the user is replacing the plaster pack 2. However, the lid 11 and a hinged gate 10 may also swing in opposite directions.

FIG. 3 shows a dispenser 1 with hinged gate 10 in its open state without the plaster packs 2. Here shoulders 7 and 8 do not prevent the movement of sheets 4a and 4b of plaster packs 2 (not shown). Thereby the user can remove the empty plaster pack 2. A new plaster pack 2 may be inserted by the user either with the gate 10 open or closed. Thus, the gate 10 may be such that, when the dispenser 1 is empty, a plaster pack 2 can be inserted into compartment 24 without opening gate 10. This may be advantageous because it saves time. Surface 19 that supports a part of sheet 4b is visible in FIG. 3.

Figure 4:
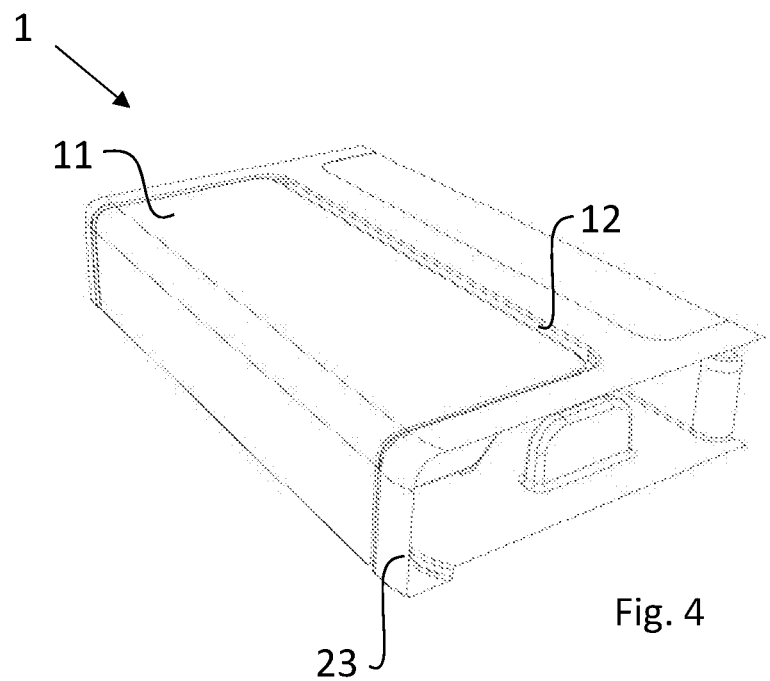
FIG. 4 is a view of a plaster dispenser with the lid closed.

FIG. 4 shows an example of the dispenser 1 with lid 11 closed.

Figure 5:
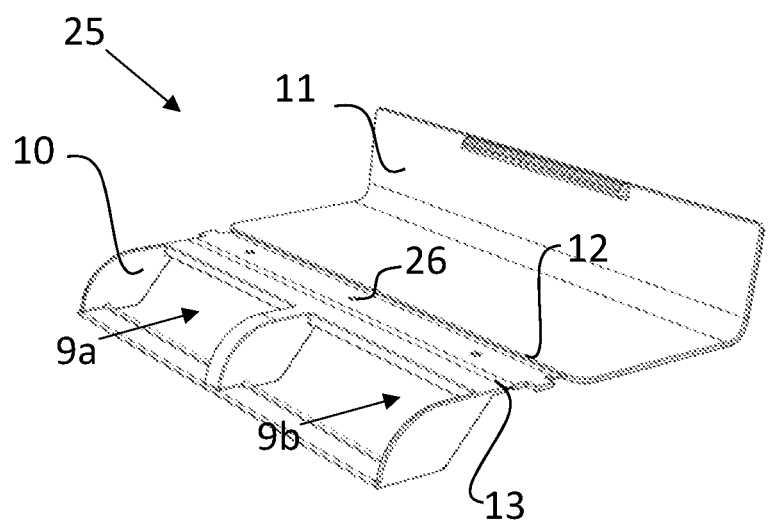
FIG. 5 is a view of a gate and the lid manufactured in one piece.

FIG. 5 shows how the gate 10 and the lid 11 can be manufactured in one piece 25, for example by moulding a polymer material. Hinges 12 and 13 are then preferably living hinges. Piece 25 may be attached to main body 23 by screwing or riveting through holes 26. However piece 25 may be attached by other means, for example with glue.

Alternatively, gate 10 and lid 11 may be manufactured as separate pieces.

Figure 6:
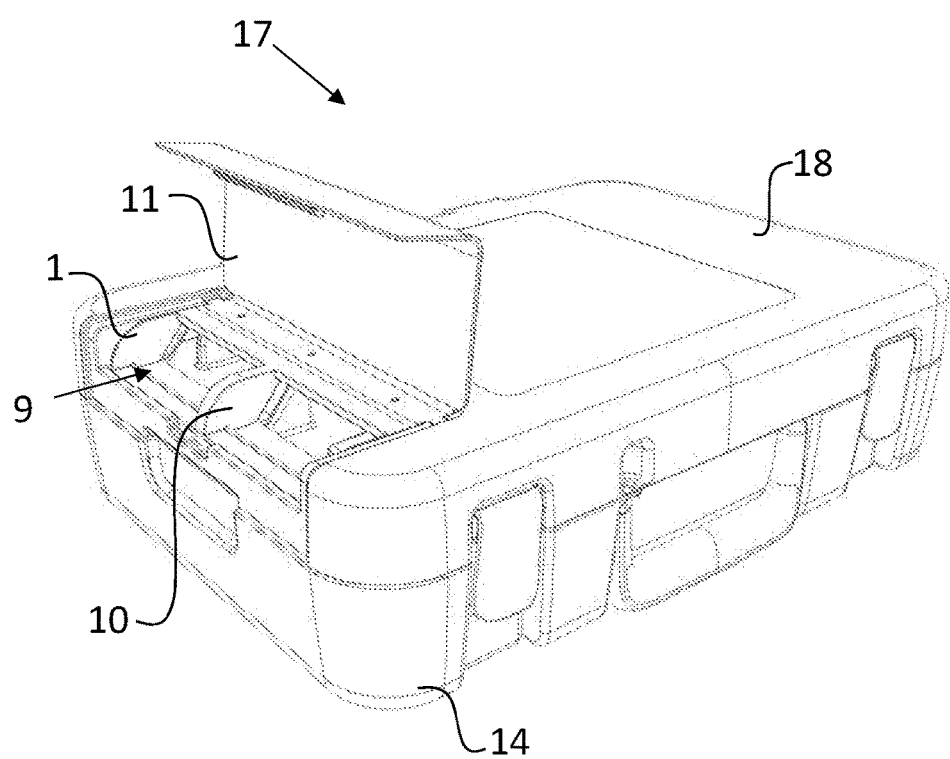
FIGS. 6-7 shows a first aid kit container.

FIG. 6 shows a first aid kit container 17 comprising a plaster dispenser 1. In FIG. 6 the first aid container 17 has the shape of a briefcase. However, the first aid kit container 17 may have any suitable shape. The first aid kit container 17 of FIGS. 6-8 has a main compartment 15 (see FIG. 8) for storing articles normally present in a first aid kit such as bandages, blood stoppers, compresses, disinfectants and pharmaceuticals. Typically main compartment 15 is larger than compartment 24 for the plaster pack 2. Main compartment 15 may have a seal that indicates whether main compartment 15 has been opened.

The first aid kit container 17 is preferable made in a stiff and yet light material such as a polymer material or a metal such as aluminum.

Figure 7:
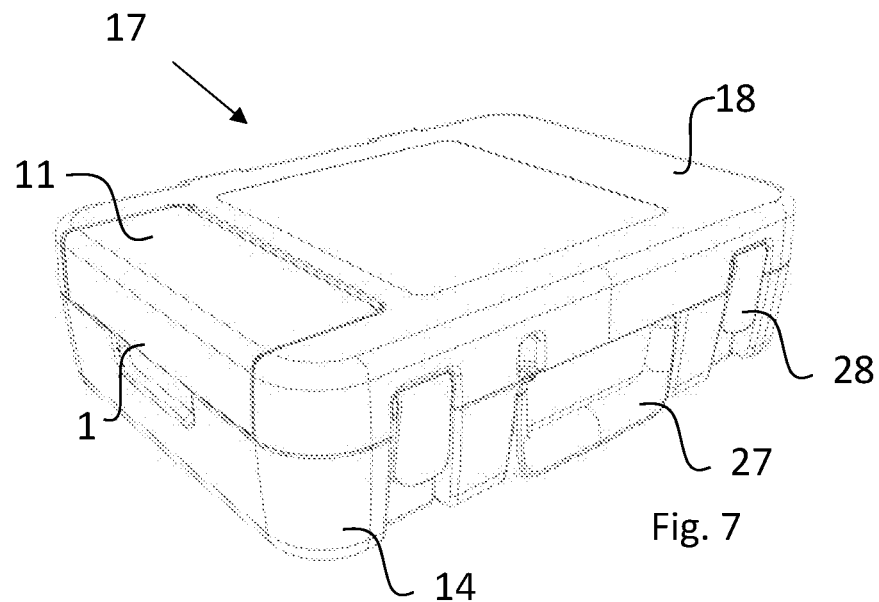
Figure 8:
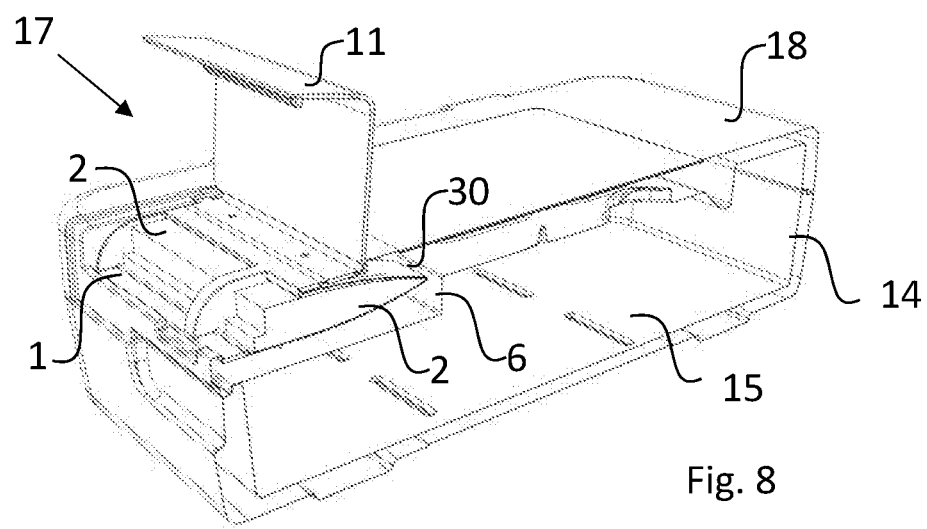
FIG. 8 shows a cross section of a first aid kit container.

The first aid kit container 17 in FIGS. 6-8 comprises two compartment forming parts 14, 18 which form the main compartment 15 (shown in FIG. 8). In FIGS. 6-7 the two compartment forming parts 14 and 18 are a main compartment box 17 and a lid 18. However, the two compartment forming parts 14 and 18 may be of equal or almost equal size, and in that case it is pointless to regard one of the two compartment forming parts 14, 18 as a "lid".

The first aid kit container 17 has an integrated plaster dispenser 1. The dispenser 1 may be integrated so that the front direction of the dispenser 1 is parallel to a wall of compartment forming parts 14 or 18. The main body 23 of the dispenser 1 may be adjacent to or integrated into a wall of the compartment forming parts 14 or 18. Certain parts of the dispenser 1, for example wall 6, surface 19 and side guides 29 may be parts of compartment forming parts 14 or 18.

The dispenser 1 is preferably arranged in the first aid kit container 17 so that opening 9, gate 10 and main opening 31 are accessible from the outside of the main compartment 15 of first aid kit container 17. Thus it is not necessary to access the main compartment 15 of the first aid kit container 17 in order to access the plasters 3 or to open the gate 10 to change the plaster pack 2. Thus plaster dispenser 1 is preferably arranged in the first aid kit container so that the opening 9, gate 10 and main opening 31 can be accessed without opening the main compartment 15, for example by opening lid 18.

When the opening 9, gate 10 and main opening 31 are accessible from the outside of the main compartment 15 of the first aid kit container 17, the dispenser 1 preferably has a lid 11 that protects the plasters 3 from dirt and moisture. The outer surface of lid 11 of dispenser 1 is, when closed, preferably continuous or almost continuous with outer surface the compartment forming parts 14 18 of first aid kit container 17, for example continuous or almost continuous with outer surface of lid 18 as shown in FIG. 7.

The plaster dispenser 1 may preferably be integrated into a lid 18 of the main compartment 15. An advantage with this is that the plasters 3 will be easily accessible since the lid 18 of the first aid kit container 17 is often facing towards the user, for example when the first aid kit container 17 is lying on a surface, as shown in FIG. 6, for example a table. Preferably the dispenser 1 is arranged such that the front direction of the dispenser 1 is parallel to the plane of the lid 18, examples of which are shown in FIGS. 6 and 8. This has the advantage that the dispenser 1 fits within the thickness of the lid 18.

The dispenser 1 may be inserted in a hollow space in a compartment forming part 14, 18 preferably the lid 18.

As mentioned above certain parts of the dispenser 1, for example wall 6, surface 19 and side guides 29 may be parts of the compartment forming parts 14, 18 in particular the lid 18, as seen in FIG. 8. The first aid kit container 17 with the integrated dispenser 1 may thus be such that is produced by two pieces of a polymer material: a first piece of polymer material forming a compartment forming part 14, 18 (preferably the lid 18) and the compartment 24 for the plaster pack 2, and one piece of polymer material 25 forming the gate 10 and the lid 11. Hinges 12 and 13 are then living hinges. This provides cost-efficient production.

In an even more preferred embodiment the front direction of the dispenser 1 is parallel to a hinge (not shown) of lid 18 of first aid kit container 17 as not to interfere with handle 27 or locking mechanisms 28. This is shown in FIGS. 6 and 7.

Dispenser 1 and first aid kit container 17 are preferably made in a polymer material. Polypropylene and polyethylene are preferred, in particular for manufacturing of piece 25 since these materials are particularly well suited for the manufacture of a living hinge.

Piece 25 can be manufactured by injection moulding. Another suitable material for the first aid kit container 17 is EVA (ethylene-vinyl acetate), in which case a container which is somewhat less stiff is obtained.

Dispenser 1 and first aid kit container 17 may be produced by methods known in the art. Blow moulding and injection moulding are suitable methods for production. A preferred method for producing lid 18 is blow moulding. This has the advantage of forming a hollow space 30 in lid 18 at a low cost so that hollow space 30 can house dispenser 1.

While the invention has been described with reference to specific exemplary embodiments, the description is in general only intended to illustrate the inventive concept and should not be taken as limiting the scope of the invention. The invention is generally defined by the claims.

The invention claimed is:

1. A plaster dispenser having a forward and a rearward direction, the plaster dispenser retaining a plaster pack that has a first sheet and a second sheet and a plurality of plasters in stacked relationship between the first and second sheets and each plaster having a respective longitudinal axis generally directed in the forward and the rearward direction, the plasters individually moveable in the forward direction relative to the first and second sheets independently of any of the other plasters, the plaster dispenser comprising:
   a) a compartment in which the a plaster pack is positionable, the compartment comprising:
      i) a main opening through which the plaster pack is insertable and removable from the compartment, and
      ii) a rearward wall of the compartment limiting movement of the plaster pack in the rearward direction relative to the compartment; and
   b) a gate having a closed state and an open state, the gate comprising:
      i) a first shoulder that, in the closed state of the gate and when the plaster pack is installed in the compartment, engages a forward end of the first sheet to limit movement of the plaster pack in the forward direction relative to the compartment;
      ii) a second shoulder that, in the closed state of the gate and when the plaster pack is installed in the compartment, engages a forward end of the second sheet to limit movement of the plaster pack in the forward direction;
      iii) an additional opening between the first and second shoulders that, in the closed state of the gate, aligns with the main opening such that plasters are removable from the plaster dispenser in the forward direction through the additional opening and the main opening;
      wherein, in the open state of the gate and when the plaster pack is installed in the compartment, the first shoulder disengages from the forward end of the first sheet and the second shoulder disengages from the forward end of the second sheet, and the plaster pack is removable from the compartment via the main opening by movement of the plaster pack in the forward direction.

2. The plaster dispenser according to claim 1 wherein the gate has a hinge for opening and closing the gate relative to the compartment.

3. The plaster dispenser according to claim 2 wherein the plaster dispenser has a lid that, when closed, covers the main opening and the gate.

4. The plaster dispenser according to claim 3 wherein the lid has a hinge for opening and closing the lid relative to the compartment.

5. The plaster dispenser according to claim 4 wherein the hinge of the lid is parallel to the hinge of the gate and arranged to open in the same direction.

6. The plaster dispenser according to claim 4 wherein the gate and the lid are made in one piece.

7. The plaster dispenser according to claim 6 wherein the gate and the hinged lid are made of a polymer material and wherein the hinge of the gate and the hinge of the lid are living hinges.

8. A first aid kit container, comprising:
the plaster dispenser according to claim 1; and
a main compartment separate from the compartment of the plaster dispenser, the plaster dispenser arranged relative to the main compartment of the first aid kit container so that individual plasters are removable and the plaster pack is replaceable without accessing the main compartment.

9. The first aid kit container according to claim 8 wherein the dispenser is arranged in the first aid kit container so that the additional opening of the, gate and the main opening are accessible without accessing the main compartment.

10. The first aid kit container according to claim 8 wherein the first aid kit container has a lid that provides access to the main compartment and wherein the plaster dispenser is integrated in the lid of the first aid kit container.

\* \* \* \* \*